United States Patent [19]

Eibl et al.

[11] Patent Number: 5,478,093
[45] Date of Patent: Dec. 26, 1995

[54] SURGICAL HANDPIECE

[75] Inventors: Johann Eibl, Mattighofen; Gunter Teufelberger; Johann Fersterer, both of Bürmoos, all of Austria

[73] Assignee: Dentalwerk Burmoos Gesellschaft m.b.H., Burmoos, Austria

[21] Appl. No.: 268,008

[22] Filed: Jun. 28, 1994

[30] Foreign Application Priority Data

Jun. 28, 1993 [AT] Austria ..................................... 1263/93

[51] Int. Cl.⁶ ............................. B23B 31/20; A61C 1/10
[52] U.S. Cl. .............................. 279/51; 279/50; 433/129; 606/79; 606/180
[58] Field of Search ..................... 279/50, 51; 433/127, 433/129; 606/79, 80, 180

[56] References Cited

U.S. PATENT DOCUMENTS 4,167,062   9/1979   Page, Jr. et al. ..................... 433/129

*Primary Examiner*—Steven C. Bishop
*Attorney, Agent, or Firm*—Friedrich Kueffner

[57] ABSTRACT

A handpiece for use in small-scale surgery and microsurgery, for example, oral surgery or surgery in the ear, nose and throat area includes a handpiece sleeve and a collet chuck which is rotatable about an axis and is arranged in the handpiece sleeve. The collet chuck is spring-biased and can be released by an actuating member. The collet chuck serves to hold a tool and is composed of two tubular members which are movable relative to each other along the axis of rotation of the collet chuck. A chucking lever for releasing the collet chuck is pivotable about a lever axis which is directed essentially in normal direction relative to the collet chuck axis. The actuating member includes a drive member which is movable in axial direction together with the two tubular members of the collet chuck, but does not rotate together with the tubular members. The drive member projects with a portion thereof in direction of the collet chuck axis into an undercut portion of the chucking lever.

10 Claims, 2 Drawing Sheets

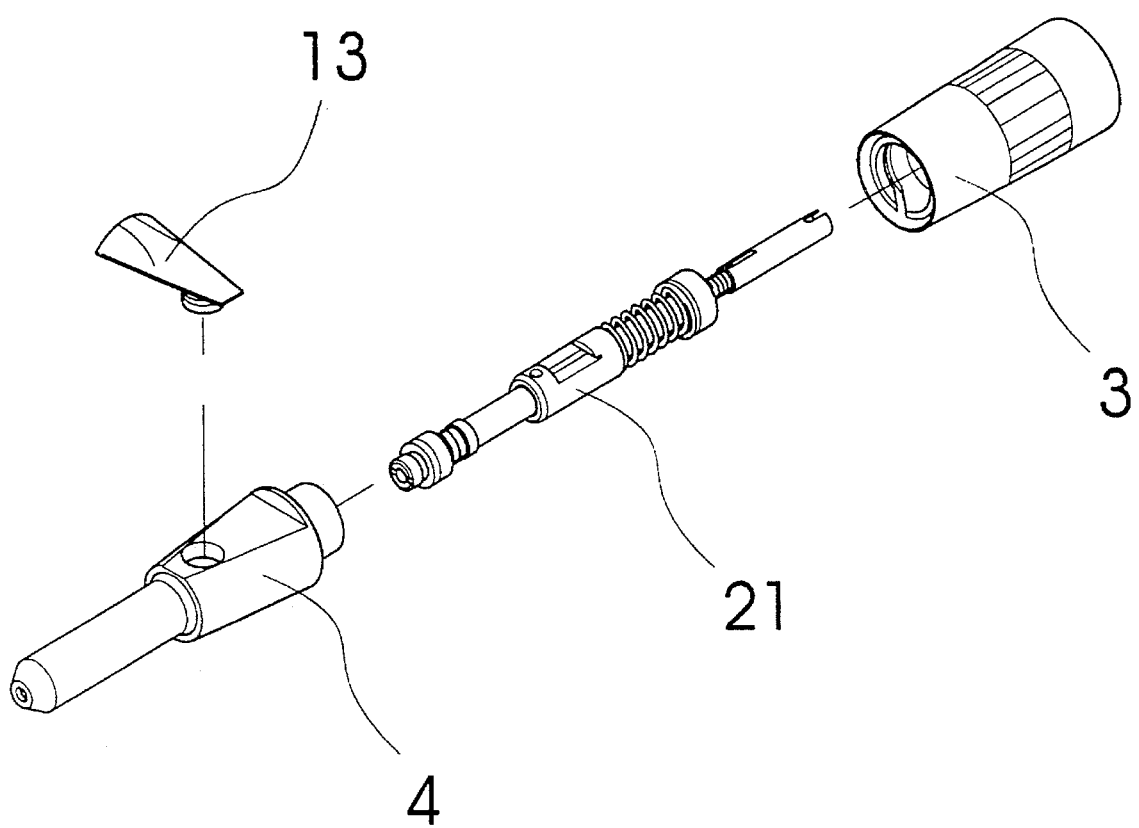

SURGICAL HANDPIECE

BACKGROUND OF THE INVENTION

1. Field of the Invention

The present invention relates to a handpiece for use in small-scale surgery and microsurgery, for example, oral surgery or surgery in the ear, nose and throat area. The handpiece includes a handpiece sleeve and a collet chuck which is rotatable about an axis and is arranged in the handpiece sleeve. The collet chuck is spring-biased and can be released by an actuating member. The collet chuck serves to hold a tool and is composed of two tubular members which are movable relative to each other along the axis of rotation of the collet chuck.

2. Description of the Related Art

Although handpieces of the above-described type are similar to dental handpieces, they cannot be compared to dental handpieces because the requirements made of surgical handpieces are substantially greater in all respects.

Thus, in the case of surgical devices, the cooling medium used is not water or a water spray, but a physiological saline solution, which increases the requirements made with respect to the corrosion resistance of all materials used in the device.

When such surgical devices are used, the operation is carried out substantially deeper below the skin or the tooth base than when dental handpieces are used, so that the danger of germs being introduced into the wound is significantly greater and particularly more dangerous, which means that the instruments are sterilized much more frequently than dental handpieces. Because the surgical handpieces are frequently heated during sterilization, the surgical handpieces are subjected to substantially greater thermal stress than dental handpieces. In addition, during sterilization there is the danger that salt is crystallized out of the saline solution which evaporates in the heat, so that there is the danger of clogging of ducts.

Finally, compared to procedures carried out by dental devices, surgical procedures usually are accompanied by severe bleeding, so that it has been found impossible in practice to reliably and permanently prevent blood from entering the instrument. Moreover, since blood enters together with saline solution, the corrosion capacity of the saline solution is increased by being mixed with the blood.

Also, because of the inaccessibility of the work areas and the depth of the operation, the external diameters of the instruments should be as small as possible for reasons of accessibility and the size of the wounds to be produced, wherein, on the other hand, the drilling or cutting efficiency is higher in the bone than in the tooth.

Therefore, it has been for a long time the wish of the users of surgical instruments to have available a surgical handpiece which can be disassembled easily, quickly and without the use of tools, in order to make it possible that the handpiece can be cleaned or sterilized frequently and thoroughly. The assembly after cleaning should be as simple as the disassembly. The instrument should have external dimensions which are comparable to those of conventional surgical handpieces or dental handpieces.

Available in this area for example, is an instrument of the above-described type as disclosed in Austrian Patent 393 788. In that instrument, a collet chuck is used for holding the tool, wherein the collet chuck is held in a closed position by the force of a spring.

For opening the collet chuck, the handpiece sleeve is rotated, which causes pressure rollers to be rotated together with the handpiece sleeve, wherein the pressure rollers roll off along a rolling plane of a pressure sleeve which facilitates a longitudinal movement of the pressure sleeve and, thus, a release of the collet chuck.

The construction of this known instrument has various disadvantages. Thus, it is necessary that the handpiece sleeve is constructed so as to be rotatable relative to the actual handpiece; the pressure rollers must be supported in such a way that the user of the handpiece does not have to apply significant forces when the collet chuck is to be tightened or clamped again; and the pressure rollers require a significant amount of space in radial direction. In order to be able to disassemble the handpiece, it is necessary to provide a special connection between the handpiece sleeve and another adjacently arranged sleeve which is called an actuating sleeve. Moreover, the positions of the two sleeves relative to each other and the position of operation of the collet chuck cannot be easily recognized.

SUMMARY OF THE INVENTION

Therefore, it is the primary object of the present invention to provide a surgical handpiece of the above-described type in which the disadvantages mentioned above are eliminated. In addition, the disassembly and reassembly of the handpiece is to be carried out quickly and simply without having to increase the external diameters of the handpiece.

In accordance with the present invention, a surgical handpiece of the above-described type includes a chucking lever for releasing the collet chuck. The chucking lever is pivotable about a lever axis which is directed essentially in normal direction relative to the collet chuck axis. The actuating member includes a drive member which is movable in axial direction together with the two tubular members of the collet chuck, but does not rotate together with the tubular members. The drive member projects with a portion thereof in direction of the collet chuck axis into an undercut portion of the chucking lever.

As a result of the features of the present invention, the chucking lever is held in its place only by the drive member, so that the aforementioned objects are met. Furthermore, when the chucking lever is of symmetrical construction, there is the advantage that opening of the collet chuck can be carried out with only one hand and equally easily for right-handed and left-handed persons, which is of particular importance for the safety of the patient when the tool becomes stuck within the patent. In collet chucks, which are to be released by rotating the sleeves, the tool would very likely break off in that situation, which would make its removal more difficult.

In accordance with a preferred feature, the drive member not only serves to axially fix the chucking lever, but also carries out the function of the member which for releasing the collet chuck displaces the two tubular members of which the collet chuck is formed.

The various features of novelty which characterize the invention are pointed out with particularity in the claims annexed to and forming a part of the disclosure. For a better understanding of the invention, its operating advantages, specific objects attained by its use, reference should be had to the drawing and descriptive manner in which there are illustrated and described preferred embodiments of the invention.

BRIEF DESCRIPTION OF THE DRAWING

In the drawing:

FIG. 2 is an exploded perspective view showing the individual components of the surgical handpiece.

DETAILED DESCRIPTION OF THE PREFERRED EMBODIMENTS

Figure 1:
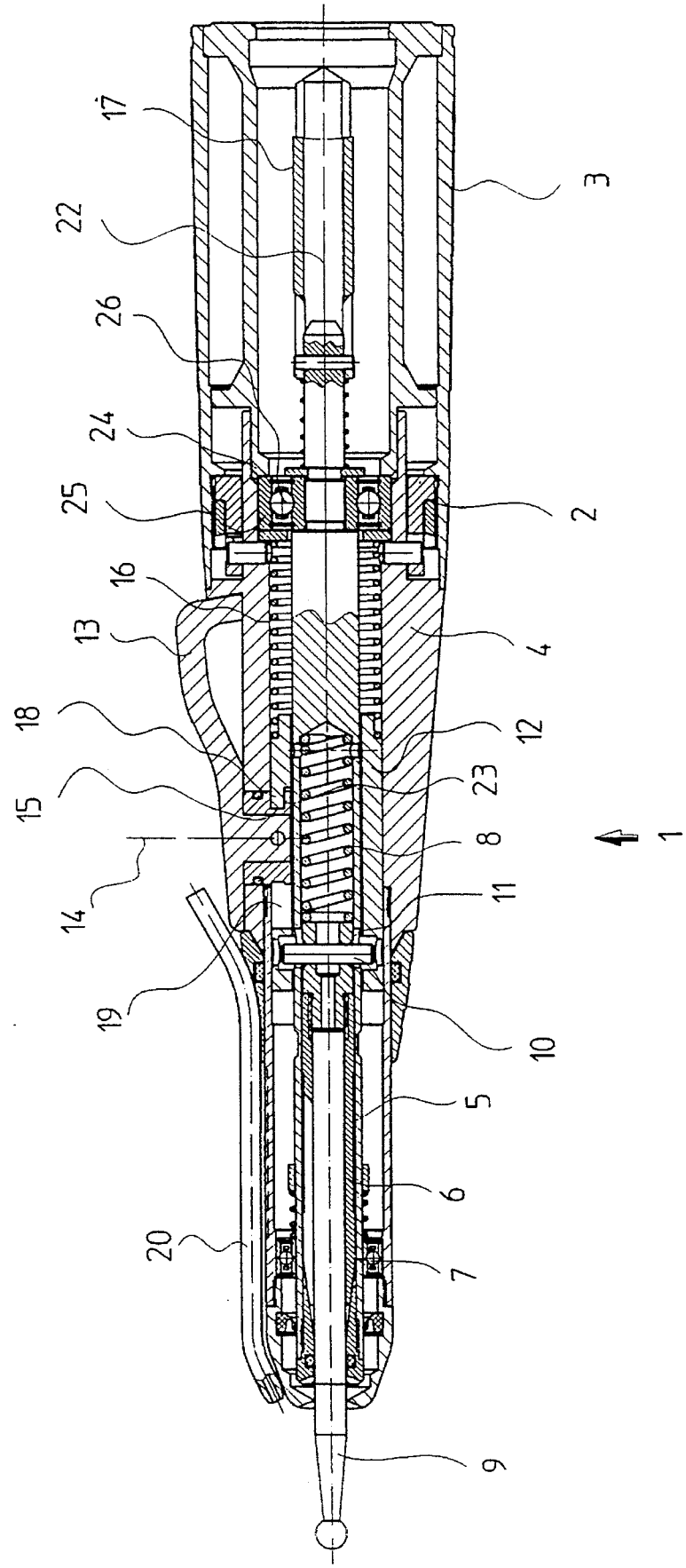
FIG. 1 is a schematic sectional view of a surgical handpiece according to the present invention.

As illustrated particularly in FIG. 1, the handpiece 1 according to the present invention includes a handpiece sleeve 4 which is connected to a coupling tube 3 by means of a bayonet-type coupling 2. The coupling tube 3 serves to connect the handpiece to a standardized supply line and may be replaced by an equivalent component.

In the illustrated embodiment, the handpiece 1 is composed of a multiple-component handpiece sleeve 4 and a spring-biased collet chuck 5 which is rotatably mounted in the handpiece sleeve 4. The handpiece 1 further includes a chucking lever 13 and a spraying device 20.

The collet chuck 5 includes two tubular members, i.e., an inner tube 6 and an outer tube 7 which are axially displacable relative to each other. The inner tube is pressed within the outer tube toward the end of the handpiece on the side of the tool as a result of the influence of a spring 8. This causes the actual collet chuck, i.e. the slotted inner tube 6, to be tensioned and the tool 9 to be held.

A transverse pin 10 is axially rigidly connected to the rotatable inner tube 6. The transverse pin 10 extends through oblong holes 11 of the also rotatable outer tube 7, wherein the ends of the transverse pin 10 project freely into an annular recess of a sleeve-shaped, non-rotatable drive member 12 so as to be rotable, but axially with only little play.

The drive member 12 can be displaced by about 30° about its axis 14 by pivoting a chucking lever 13. This is effected by means of a cam-like recess 15 of the chucking lever against the force of a holding spring 16 in axial direction toward the rear, i.e., away from the end of the handpiece on the side of the tool. As a result of this movement, the ends of the transverse pin 10, and, thus, the inner tube 6 are also displaced relative to the outer tube 7 in this direction against the force of the tensioning spring 8, and the tool 9 is released. The axis 14 is directed essentially in normal direction relative to the axis 22 of rotation of the chucking device.

For disassembling the handpiece, it is sufficient to release the bayonet-type coupling 2 between the handpiece sleeve 4 and the coupling tube 3 by rotating the two components relative to each other and, subsequently, to move the collet chuck 5 with its drive member 17 and the bearings 26, in its totality denoted as "shaft unit" 21, axially out of the handpiece, so that a projection 18 of the drive mender 12 interacting with the cam-surface 15 of the chucking lever 13 is moved out of the area of the undercut portion 23 of the chucking lever and the chucking lever can be moved out of the handpiece in the direction of its axis 14 of rotation.

In order to make this axial movement possible, it is important that, on the side of the chucking lever 13 facing the tool, the drive member 12 has a recess 19, which allows an axial displacement between the drive member and the chucking lever.

After the chucking lever 13 has been removed from the handpiece, the entire shaft unit 21 can be pulled out of the handpiece and the individual components can be cleaned and sterilized in an autoclave or in another desirable manner.

The assembly of the handpiece takes place in the reverse order. Thus, the shaft unit 21 is placed in the handpiece 1, wherein, just before reaching the position of operation of the shaft unit 21, the chucking lever 13 is pushed into its opening. Subsequently, the coupling tube 3 is again fastened to the handpiece 1 by means of the bayonet-type coupling 2, so that the axial position of the shaft unit is determined and, thus, the chucking lever 13 is held at its location.

FIG. 2 of the drawing shows the components into which the handpiece can be disassembled, i.e., the actual handpiece 1, the chucking lever 13, the shaft unit 21 and the coupling tube 3. The spraying device 20 shown in FIG. 1, which is fastened to the handpiece 1 by means of a support ring, is already removed from the handpiece shown in FIG. 2 and is not illustrated.

The present invention is not limited to the illustrated embodiment; rather, various modifications are possible. For example, instead of the bayonet-type coupling 2, a threaded connection or another connection can be provided.

The collet chuck may also be of a different construction. A large variety of configurations and modifications of dental handpieces are known in the art. However, the construction of the illustrated embodiment is preferred because of the secure support imparted to the tool. Other changes are possible, for example, by replacing the tubular members in such a way that the outer tube 7 is displaceable relative to the handpiece sleeve 4 and the inner tube 6 is not displaceable. This makes it possible to eliminate the bolt 10 and the annular recess of the drive member 12, but it is then necessary that the outer tube 7 is displaceably mounted in the handpiece sleeve 4.

It is important that the chucking lever 13 secures the axial position of the two tubular members 6 and 7 and, thus, the axial position of the collet chuck 5 and that the drive member 12 secures the axial position of the chucking lever 13. In the illustrated embodiment, this is achieved by the above-described engagement of the cam-like surface 13 and the control projection 18 including the undercut portion 23. Of course, the cam may also be constructed so as to be separate from the undercut portion.

The final fixation of the shaft unit 21 can be effected in different ways. The use of the coupling tube 3 for this purpose reduces the structural size and the number of components required. For example, it is possible to provide a fastening ring on which is provided a transition to the drive unit. When the front ends of such drive units are of suitable construction, they can additionally assume the support function of the individual handpiece components, so that the handpiece is also disassembled when it is removed.

The spraying device may also be integrated in the handpiece or even in the interior of the tool. A lighting device may be provided for illuminating the work area.

The invention is not limited by the embodiments described above which are presented as examples only but can be modified in various ways within the scope of protection defined by the appended patent claims.

We claim:

1. A handpiece for use in small-scale surgery or microsurgery, for example, oral surgery or surgery in the ear, nose and throat area, the handpiece comprising a handpiece sleeve, a collet chuck rotatably mounted in the handpiece sleeve, the collet chuck comprising two tubular members, the two tubular members being displaceable relative to each other along an axis of rotation of the collet chuck, an actuating member comprising a chucking lever for releasing the collet chuck, the chucking lever being pivotable about a lever axis extending essentially in normal direction relative to the axis of rotation of the collet chuck, the actuating member further comprising a non-rotatable drive member, the drive member being displaceable in axial direction together with the two tubular members of the collet chuck, the chucking lever having an undercut portion, the drive member having a portion projecting in the direction of the axis of rotation of the collet chuck into the undercut portion of the chucking lever.

2. The handpiece according to claim 1, wherein the drive member is of single-piece construction.

3. The handpiece according to claim 1, wherein the chucking lever has a cam-like surface in an area of the undercut portion, and wherein the portion of the drive member comprises a control projection, the control projection engaging in the cam-like surface for releasing and clamping the collet chuck.

4. The handpiece according to claim 3, wherein the cam-like surface is symmetrical with respect to a plane defined by the lever axis and the axis of rotation of the collet chuck, such that the chucking lever is pivotable to both sides for releasing the collet chuck.

5. The handpiece according to claim 1, wherein the chucking lever is pivotable about a pivoting angle of approximately 30°.

6. The handpiece according to claim 1, wherein the collet chuck comprises a rotatable drive member and bearings for the collet chuck, and wherein the collet chuck, the actuating member, the rotatable drive member and the bearings form a shaft unit, further comprising a coupling tube connected to the handpiece sleeve, the position of the shaft unit in the handpiece sleeve being determined by the coupling tube.

7. The handpiece according to claim 6, comprising a bayonet-type coupling for connecting the coupling tube to the handpiece sleeve, further comprising at least one pressure element in the coupling tube, the shaft unit having a non-rotatable component, wherein the pressure element presses in axial direction against the non-rotatable component of the shaft unit toward a tool.

8. The handpiece according to claim 6, wherein the bearing between the handpiece sleeve and the shaft unit is arranged in axial direction between the chucking lever and the coupling tube.

9. The handpiece according to claim 8, further comprising a compression spring mounted between the bearing and one of the chucking lever and the drive member.

10. The handpiece according to claim 9, wherein the drive member comprises a drive member sleeve, the drive member sleeve engaging the cam-like surface of the chucking lever for releasing the collet chuck, and wherein the drive member sleeve has at the chucking lever a recess on a side facing a tool.

* * * * *